United States Patent [19]

Ammann

[11] Patent Number: 4,944,941

[45] Date of Patent: Jul. 31, 1990

[54] METHODS AND COMPOSITIONS FOR THE TREATMENT OF LUNG CONDITIONS

[75] Inventor: Arthur J. Ammann, San Rafael, Calif.

[73] Assignee: Genentech, Inc., South San Francisco, Calif.

[21] Appl. No.: 83,605

[22] Filed: Aug. 7, 1987

[51] Int. Cl.⁵ .................. A61K 37/66; A61K 37/00
[52] U.S. Cl. .................................... 424/85.5; 424/85.1
[58] Field of Search ................... 424/85.1; 442/85.5

[56] References Cited

U.S. PATENT DOCUMENTS

| | | | |
|---|---|---|---|
| 4,522,811 | 6/1985 | Eppstein et al. | 424/85.5 |
| 4,650,674 | 3/1987 | Aggarwa et al. | 424/85.5 |
| 4,762,791 | 8/1988 | Goeddel et al. | 435/240.2 |
| 4,774,085 | 9/1988 | Fidler | 424/85.5 |

FOREIGN PATENT DOCUMENTS

| | | |
|---|---|---|
| 82466187 | 11/1987 | Australia . |
| 177910 | 4/1986 | European Pat. Off. . |
| 0257956 | 2/1988 | European Pat. Off. . |

*Primary Examiner*—Blondel Hazel
*Attorney, Agent, or Firm*—Carolyn R. Adler

[57] ABSTRACT

Disclosed are improved methods for the treatment of lung membrane diseases such as respiratory distress syndrome (RDS) or idiopathic RDS, employing compositions including therapeutically effective amounts of gamma interferon and/or tumor necrosis factor (TNF), each alone or in combination with corticosteroids, preferably employing recombinant human gamma interferon and/or TNF. Individuals, including adults or children, are administered amounts of these agents that are generally effective to induce the lungs of affected individuals to produce one or more surfactant components, including both phospholipid and surfactant protein substituents.

15 Claims, 1 Drawing Sheet

METHODS AND COMPOSITIONS FOR THE TREATMENT OF LUNG CONDITIONS

BACKGROUND OF THE INVENTION

1. Field of the Invention

The present invention relates to the treatment of lung conditions, and in particular, the treatment of lung conditions involving reduced or suppressed levels of endogenous surfactant production, through the use of gamma interferon-containing compositions.

2. Description of the Related Art

Millions of individuals worldwide are afflicted annually with debilitating lung diseases. The lives of many of these individuals will be lost, and the lives of the rest made much less comfortable, by diseases of the lung. Respiratory distress syndromes (RDS), which comprise a significant proportion and variety of lung diseases, are particularly troublesome due to the high mortality rates associated with the various types of RDS disease. For example, in adult respiratory distress syndrome (ARDS), a mortality rate of greater than 50% is observed. Moreover, in premature infants a similar mortality rate is seen in Hyaline membrane disease, at least in smaller premature infants.

Normal lung function depends on the presence of an alveolar lining layer with properties that permit alternate increases and decreases in surface tension, thus allowing continuous sorption and desorption of respiratory gases. To function properly in the exchange of gases, and to maintain its structural integrity, the alveolar lining must retain its elasticity. The principal mechanism employed by the body to maintain alveolar elasticity is through the production of surfactant, primarily by type II alveolar cells. When these cells fail to produce a sufficient amount of surfactant, or one or more of its components, the alveolar elasticity is decreased or lost, resulting in reduced gas exchange and often alveolar collapse.

Respiratory distress syndrome is a descriptive term that has been applied to many acute, diffuse infiltrative lung lesions of diverse etiologies when they are accompanied by arterial hypoxemia. Diseases classified generally as respiratory distress syndromes range from adult respiratory distress syndromes (ARDS) to a neonatal form, termed variously as idiopathic RDS or hyaline membrane disease. The term RDS is applied to the various forms because of several clinical and pathologic similarities between such acute illnesses in adult and neonatal forms. However, in the neonatal form, immaturity of alveolar surfactant production and a highly compliant chest wall are primarily involved in the pathophysiology, whereas in the adult forms, alveolar surfactant changes are secondary to the primary process, and the chest wall is not compliant.

Adult respiratory distress syndrome includes diseases of numerous etiologies, ranging from diffuse pulmonary infection (e.g., viral, bacterial, fungal, pneumocystis, etc.), inhalation of toxins and irritants, narcotic overdose and other drug effects, immunologic responses, endotoxin shock, nonthoracic trauma with hypotension, and even postcardiopulmonary bypass (e.g., "pump lung" or "post-perfusion lung"). Regardless of the etiology, ARDS is invariably associated with increased liquid in the lungs. Moreover, certain of these conditions have as a secondary process an underlying reduction in surfactant content of one or more surfactant components. It is these conditions involving a reduction in lung surfactant with which the present invention is concerned.

While decreased surfactant content plays a role in RDS and ARDS of various etiologies, this problem is symptomatic of RDS in premature infants. In this disease, often referred to as hyaline membrane disease or idiopathic RDS, surfactant deficiency is generally due to its "immaturity" with respect to the synthesis of one or more surfactant components. While the disease affects greater than 60% of very premature children, idiopathic RDS is not limited exclusively to premature infants and various forms may afflict term children.

In contrast to ARDS, idiopathic RDS has a more restricted etiology, occurring primarily in infants who are premature, but also in infants having a familial disposition to RDS, those with acidosis, C-section infants, and infants suffering from intrapartum asphyxia. There has been no indication, however, that idiopathic RDS is caused by exogenous trauma or infections of the lungs per se, viral or otherwise. In all cases of idiopathic RDS, immaturity of alveolar surfactant production or overall non-production appears to be a primary cause. In such infants, alveolar atelectasis, hyaline membrane formation and interstitial edema make the lungs less compliant, requiring greater pressure to expand the small alveoli and airways. Deficient synthesis or release of surfactant, together with small respiratory units and compliant chest wall, results in atelectasis, rapid respiratory rate, etc. Pulmonary blood flow is thus reduced with ischemic injury to lecithin producing cells and the vascular bed, resulting in an effusion of proteinaceous material into the alveolar spaces.

Natural lung surfactant is a lipid composition which includes a complex mixture of primarily phospholipids and proteins, with lipids making up about 99% of the composition. The lipid component is composed mainly of dipalmitoyl phosphatidylcholine (dipalmitoyl lecithin), phosphatidyl glycerol, phosphatidyl ethanolamine and other lipids and phospholipids. The protein components of surfactant, required for full surfactant properties, include primarily two apoprotein species. The larger of these two proteins is a species demonstrating size heterogeneity of between about 29,000 and 36,000 daltons. (see, e.g., King et al. (1972), *Am. Jrnl. Physiol.*, 223:715-726; PCT publication number WO 86/03408). A second protein species, also thought to be a mixture, has been identified in surfactant as having a molecular weight in the range of about 6 to 14 kilodaltons. In both cases, the size heterogeneity exhibited by these proteins is believed to represent, at least in part, varying degrees of glycosylation of peptide species. Importantly, the presence of these two apoproteins has been shown to enhance the rate of surface-film formation. (see, e.g., Whitsett et al. (1986), *Pediatr. Res.*, 20:460; Avery et al. (1986), *New Engl. Jrnl. Med.*, 315:825).

The treatment of respiratory distress diseases, including both adult and idiopathic RDS, has traditionally been limited to supportive care including, for example, oxygen administration or even mechanical ventilation. Forced ventilation is not only an inadequate treatment in most severe cases of RDS and surfactant-deficiency RDS, it places mechanical stress on the lungs and diaphragm and can lead to severe alveolar trauma or even pneumothorax.

More recently, some success in the treatment of RDS, particularly idiopathic RDS, has been reported with both natural and synthetic surfactants (see, e.g., Kwong et al. (1985), *Pediatrics*, 76:585; Mervitt et al. (1986), *New Engl. Jrnl. Med.*, 315:785; Whitsett et al., supra). In these instances, various surfactant mixtures are typically applied directly to lung tissues by installation in an attempt to replenish lung surfactant contact exogenously. Corticosteroids have also found some utility in the treatment of RDS, particularly when administered to expectant mothers of premature infants (see, e.g., Ballard et al. (1980), *J. Pediatr.*, 97:451; Papageorgiou et al. (1981), *Pediatrics*, 67:416).

Unfortunately, present treatment protocols such as the foregoing are far from ideal or even adequate in the treatment of all cases of RDS. While shown to be effective in certain instances, both natural and synthetic surfactants are expensive, often difficult to prepare, and not always successful. Moreover, other than natural extracts of human tissues or those employing human recombinant proteins, most preparations are devoid of human surfactant proteins. Corticosteroid therapy is also undesirable under certain circumstances, for example, as a direct treatment in premature infants or in patients sensitive to corticosteroids. In any case, there is currently a great need for additional approaches to the treatment of lung diseases, and particularly, to the treatment of diseases or conditions wherein there is a need to increase lung surfactant content.

SUMMARY OF THE INVENTION

Recognizing the foregoing and additional disadvantages present in the art, it is a general object of the present invention to provide improved methods and compositions for the treatment of lung diseases, particularly diseases involving a reduced level of one or more components of surfactant, such as various forms of respiratory distress syndromes. In particular, it is an object to provide methods and compositions for treating idiopathic RDS or hyaline membrane disease, either by administration of pharmaceutical compositions to an expectant mother, e.g., by intra-uterine administration, or directly to an infant.

It is an additional object of the invention to provide methods for increasing the overall lung surfactant content in individuals suffering, for example, from conditions resulting in reduced surfactant production or alveolar responsivity.

In particular, it is an object to provide methods and compositions for stimulating a patient's own body to produce endogenous surfactant components (that is, surfactant produced by the patient's own body), thus avoiding a need to administer exogenous surfactant (that is, surfactant produced outside the patient's body) where it is unavailable.

In a general and overall sense, the invention is concerned with the treatment of membrane diseases through the administration of gamma-interferon (IFN-gamma) and/or tumor necrosis factor (TNF) containing compositions. In that these agents act by directly stimulating the lung to produce surfactant components, including, in preferred embodiments, both lipid and protein components, it should be appreciated that utility of the invention is not limited to the treatment of respiratory distress syndromes, or idiopathic RDS. Rather, the invention is concerned generally with the treatment of any condition where an enhanced surfactant production or content is desired or needed.

As used herein, "gamma interferon" refers variously to all forms of gamma interferon as are known to be biologically active in accepted IFN-gamma assays, such as by inhibition of encephalomyocarditis virus replication in A549 cells (human lung carcinoma cell line) induction of class II antigens, heat lability, or neutralization by antibodies having immunoreactivity for IFN-gamma but not IFN-alpha or beta, and is meant to include IFN-gamma in a mature, pro, met or des (1-3) form, whether in the form of natural human gamma interferon (hIFN-gamma), recombinant human gamma interferon (rIFN-gamma) or related IFN-gamma substances (e.g., non-human IFN-gammas). Moreover, TNF, as employed herein, refers, in general, to the various forms of TNF which exhibit one or more biologic properties of tumor necrosis such as tumor cell lysis, inhibition of infectious agents, class II antigen induction and neutralization by antibody to TNF-alpha or TNF-beta (lymphotoxin) but not by antibodies to other cytokines. In a pharmacologic sense, in the context of the present invention a therapeutically effective amount of IFN-gamma or TNF refers to that amount effective to induce the production of one or more surfactant components by the individual's lungs.

In the practice of the invention, compositions which include a therapeutically effective amount of gamma interferon and/or TNF are administered to individuals in need of an increased lung surfactant content. Typically, a sufficient dose or dosages are administered to such individuals in overall amounts effective to stimulate lung cells, for example, alveolar type II cells, to produce surfactant components, including one or more, preferably both, phospholipid and protein components.

Accordingly, in certain embodiments of the invention, a method is provided for treating an individual to increase the surfactant content of the individual's lungs, wherein the method includes identifying such an individual whose lungs may be in need of an increased level of surfactant and administering to the individual a composition which includes a therapeutically effective amount of gamma interferon and/or TNF, either through parenteral administration or direct application to the lungs.

As is known in the art, the identification of an individual who may be in need of an increased lung surfactant content may be made by a number of accepted diagnostic procedures. One such technique involves direct endoscopic examination perhaps accompanied by microscopic examination of lung tissue. Surfactant-deficient lung tissue will generally appear deep purplish red, often with regions of hemorrhage and extensive atelectasis, and hyaline membrane formation, particularly in idiopathic RDS. Clinically, the earliest signs are generally tachypnea, which may not be seen in idiopathic RDS until an hour or so post partum, often followed by dyspnea and generalized cyanosis and pallor. Perhaps a more convenient detection method under certain circumstances is through the use of pH, $pO_2$ and $pCO_2$ levels in an arterial blood sample (arterial blood gases). In patients suffering from severe surfactant deficiencies, $pO_2$ levels will generally be depressed to well below 60 mm/Hg, with rising $pCO_2$ levels and often pronounced acidosis.

For the identification of idiopathic RDS, the preferred methods is that described generally by Gluck et al., (1971) *Am. Jrnl. Obs. Gyn.*, 109:440, incorporated herein by reference. Their work pioneered the use of phospholipid analysis in amniotic fluid to predict the likelihood of hyaline membrane disease before birth. They noted that the proportion of different phospholipids in amniotic fluid changed with gestation: the concentrations of lecithin and sphingomyelin are equal in midgestation, but after 34 to 36 weeks there is twice as much lecithin as sphingomyelin; this change parallels the maturation of the lung. Their work has led to the widespread use of the lecithin-sphingomyelin (L/S) ratio for predicting which fetuses will develop hyaline membrane disease upon delivery.

Another more rapid test for lung maturity is the foam stability or shake test described by Clements et al., (1972) *New England Jrnl. Med.*, 286:1077. The rationale of this test is based upon the ability of pulmonary surfactant to form surface film capable of supporting the structure of a foam.

While the present invention is directed in general to the treatment of any condition wherein an increased lung surfactant level is desired, the use of gamma interferon is particularly advantageous in the treatment of idiopathic RDS, wherein therapeutic compositions including gamma interferon and/or TNF are administered to expectant mothers, e.g., by direct systemic or in utero administration, or directly to afflicted infants in effective amounts. It is proposed that a direct systemic administration to an expectant mother will be effective based on recent findings that IFN-gamma appears to cross the placenta (see, e.g., Murasko et al. (1986) *Virology*, 106:148).

For the treatment of diseases of the lung in an adult it is generally recommended that a total daily dose of between about 0.01 and about 2.0 mg/m$^2$ of gamma interferon be administered, preferably between about 0.2 and about 0.5 mg/m$^2$. This corresponds to between about 0.015 and 3.0 mg/day/patient for a mature adult (approx. 5'9", 70 Kg), or approximately 0.0002 to 0.043 mg/kg/day (body surface area approximately 1.5 m$^2$). In the case of infants and premature infants, it will be appreciated that a much smaller overall dose will be indicated, albeit at a similar mg/m$^2$ dose, in that infants have a somewhat lower weight/m$^2$ body surface area. In general, a dose range of 0.01 to 2.0 mg/m$^2$/day for an infant will be equivalent to about 0.0003 to about 0.06 mg/kg/day (wherein the body surface area of the infant is less than about 0.5 m$^2$). However, it will be appreciated by those of skill that dosages and treatment regimens will typically be modified according to the attendant circumstances and medical conditions.

For the purposes of the present invention, useful dosages of TNF, whether TNF-alpha or beta, will range from about 1 to about 400 mcg/m$^2$/day, either alone or, more preferably, in combination with IFN-gamma. In general, the dosing considerations for TNF will be similar to those discussed above in connection with IFN-gamma. Moreover, as with IFN-gamma doses, it will be appreciated by those of skill in the art that dosages and treatment regimens will typically be modified according to the particular circumstances.

In general, upper doses will be limited by the degree of untoward effects exhibited by the drug in the individual patient. The most common, and generally dose-limiting, side effects of IFN-gamma therapy are constitutional symptoms, including fever, chills, fatigue, myalgias, headaches, and the like. In some instances, granulocytopenia as well as hepatic transaminase elevations have been found to be dose limiting. Accordingly, upper dose limits are most preferably determined in relation to relevant circumstances such as the degree of discomfort experienced by the patient, taking into consideration the severity of the particular case and the response shown by the patient at lower doses. Thus, in some patients and/or in certain severe cases, it may be determined that larger or smaller doses than the foregoing general ranges are appropriate.

The untoward effects of TNF are similar both in kind and severity of those of IFN-gamma, and include generally fever, chills, headache and fatigue. As with IFN-gamma, these side effects of TNF are frequently found to be dose limiting. Other occasional side effects include nausea, vomiting and diarrhea. Moreover, other potentially dose limiting side effects include hypotension, hematologic toxicity (granulocytopenia and thrombocytopenia) and neurologic toxicity (ischemic events).

Compositions are formulated employing gamma interferon, preferably from recombinant sources such as described in U.S. Pat. No. 4,762,791, incorporated herein by reference, and/or TNF, preferably recombinant type TNF such as described in U.S. Pat. No. 4,650,674, incorporated herein by reference, typically in combination with a pharmaceutically acceptable diluent or excipient for parenteral administration. However, as noted above, other forms of IFN-gamma may be employed as well, such as naturally-derived hIFN-gamma, or more preferably, des (Cys$_1$-Tyr$_2$-Cys$_3$) IFN-gamma, (e.g., see application publication number 146,354A, incorporated herein by reference). Moreover, other biologically active forms of TNF, such as TNF-beta (lymphotoxin), are known and all such forms may be employed. Suitable carrier vehicles and their formulation are described, for example, in *Remington's Pharmaceutical Sciences*, 16th ed., 1980, Mack Publishing Co., edited by Oslo et al., incorporated herein by reference. Suitable carriers include sterile aqueous solutions including stabilizing agents, e.g., buffers and other protein and pH-stabilizing agents, salts and the like. Typically, sterile aqueous gamma interferon and/or TNF compositions include a dose concentration of between 0.2 and 2.0 mg/ml with respect to IFN-gamma, and about 0.1 to 1.0 mg/ml with respect to TNF, to allow for the administration of convenient amounts.

IFN-gamma and/or TNF compositions of the present invention are typically provided in the form of a sterile lyophilized powder having included therein appropriate salts, etc., to which sterile water may be added to render a final desired concentration, depending on the dose and route which will be employed.

In general, it has been found that the tolerated dose of IFN-gamma is somewhat dependent on the route of administration. Thus, for example, in the case of IFN-gamma, the maximally tolerated dose (MTD) for daily i.m. injection in many patients will generally be on the order of about 0.25 to about 0.5 mg/m$^2$/day or higher, while the MTD for daily 24-hour intravenous infusion is about 0.01 to about 0.025 mg/m$^2$/day. Similarly, the MTD for TNF is also somewhat dependant on the route of administration. For example, the MTD for i.m. or subcutaneous TNF administration ranges from about 50 to 75 mcg/m$^2$ and higher in some patients, whereas it is about 200 mcg/m$^2$ for bolus i.v. administration.

It will be appreciated that when administered intramuscularly (i.m.), a somewhat longer, more sustained but somewhat reduced plasma level is typically obtained relative to similar intravenous (i.v.) doses. Following i.v. administration an initial spiking of plasma levels is followed by a relatively fast plasma clearance. The difference in routes is reflected in divergent half-lives, e.g., i.m. IFN-gamma generally exhibiting a half-life up to or more than 10 times greater than the i.v.

half-life. Accordingly, where i.v. administration is desired, it is generally recommended that the selected dose be administered by daily infusion over a six to eight hour period. Where an i.m. route is chosen, it is generally preferable to administer the daily dosage in one or more daily injections.

In certain embodiments, compositions are administered to lung tissue by means of direct instillation into the lungs, indirectly into amniotic fluid or through the use of a nasal spray. Instillation is achieved generally by introducing IFN-gamma compositions into the affected individual's lungs through an endotracheal tube using, for example, a syringe and Brodie adapter. In the practice of such instillation methods it will be particularly beneficial to include in the compositions a certain amount of surfactant, either natural or artificial, from recombinant or tissue sources, to serve both as a convenient carrier and as a adjunct to therapy.

Typical surfactants useful in the practice of such embodiments include natural surfactants, such as the human surfactant described by Merrit et al., supra, or human amniotic extract as described by Hallman et al. (1983), *Pediatrics*, 71:473–482, the calf lung surfactant extract of Kwong et al., supra, or Fujwara et al. (1980), *Lancet*, 1:55. Artificial surfactants such as, those described by Durand et al. (1985), *J. Pediatr.*, 107:775 or U.S. Pat. No. 4,312,860, or surfactants which includes recombinant surfactant protein(s) as described in PCT application WO 86/03408, all incorporated herein by reference, may also be employed. In certain instances it may be further desirable to encapsulate the IFN-gamma and/or TNF into liposomes or lipid capsules, in that it is believed that such preparations provide additional benefits including, for example, more sustained levels and continuous release of pharmaceutically active components at the site of action, e.g., at the locus of type II alveolar cells.

BRIEF DESCRIPTION OF THE DRAWINGS

FIG. 1 illustrates graphically the induction of phosphatidylcholine synthesis by various agents on human lung explants in organ culture. Shown are the effects of Dexamethasone (DEX; 10 nmolar), rIFN-gamma (I; with I/1, I/10 and I/100, representing 0.1, 1.0 and 10 ng/ml of des (1-3) rIFN-gamma, respectively), Tumor Necrosis Factor (T; with T/1, T/10 and T/100, representing 0.1, 1.0 and 10 ng/ml, respectively), dexamethasone +IFN-gamma (DEX+I, at 10 nmolar and 10 ng/ml rTNF-alpha, respectively), control at time of experiment (CONT) and control prior to experiment (PRE) administrations.

DETAILED DESCRIPTION OF THE PREFERRED EMBODIMENTS

A. Human Immune Interferon

Human interferons can be classified in three groups on the basis of different antigenicity, biological and biochemical properties.

The first group comprises a family of leukocyte interferons (alpha-interferon, LeIF or IFN-alpha), which are normally produced mainly by constituent cells of human blood upon viral induction. These have been microbially produced and found to be biologically active (Goeddel et al. (1980), *Nature*, 287:411; Goeddel et al. (1981), *Nature*, 290:20; and Yelverton et al. (1981), *Nucl. Acids Res.*, 9:731). Their biological properties have prompted their use in the clinic as therapeutic agents for the treatment of viral infections and malignant conditions (see, e.g. Gutterman et al. (1980), *Annals of Int. Med.*, 93:399).

In the second group is human fibroblast interferon (beta-interferon, FIF or IFN-beta), normally produced by fibroblasts upon viral induction, which has likewise been microbially produced and found to exhibit a wide range of biological activities (Goeddel et al. (1980), *Nucl. Acids Res.*, 8:4057). Clinical trials also indicate its potential therapeutic value. The leukocyte and fibroblast interferons exhibit very clear similarities in their biological properties despite the fact that the degree of homology at the amino acid level is relatively low. In addition, both groups of interferons contain from 165 to 166 amino acids and are acid stable proteins.

The human immune interferon (gamma-interferon, IIF or IFN-gamma), to which this invention is directed, is, in contrast to the alpha- and beta-interferons, pH 2 labile, is produced mainly upon mitogenic induction of lymphocytes and is also clearly antigenically distinct from alpha and beta IFN's. Until recently, human immune interferon could only be detected in very minor levels, which evidently hampered its characterization. Human immune interferon was reported to have been partially purified by Yip et al. (1981), *Proc. Natl. Acad. Sci. U.S.A.*, 78:1601, from natural sources. More recently, the gene encoding human gamma interferon has been cloned and expressed, resulting in its ready availability to those in the art. A full description of the cloning of the human gamma interferon gene, and the subsequent preparation of recombinant IFN-gamma suitable for use herein, is given in EPO patent application publication 0077670.

IFN-gamma is a T-cell-derived lymphokine which has been shown to function as a differentiation factor, an immune regulator with macrophage activator effects, and as an antimicrobial agent against intracellular protozoa and bacteria (see, e.g., Kurzrock et al. (1985), *Cancer Res.*, 45:2866–2872). This spectrum of activity of IFN-gamma has led to a potential therapeutic role for this material in patients with cancer, viral diseases and opportunistic infections. Prior to the availability of the above-referenced recombinant sources, reported clinical studies employing IFN-gamma preparations were limited to preliminary pharmacokinetic evaluation of native IFN-gamma, which was available in only limited amounts and of limited purity (see, e.g., Gutterman et al. (1984), *Cancer Res.*, 44:4164). However, the availability of recombinant IFN-gamma has allowed for the first time, clinical evaluation of purified IFN-gamma compositions.

To date clinical trials of IFN-gamma have involved primarily phase I trials of IFN-gamma pharmacokinetics and toxicity pharmacology in cancer patients (see, e.g., Kurzock et al. (1985), *Cancer Immunol. Immunother.*, 20:193; Kurzock et al. (1986), *Jrnl. Clin. Oncol.*, 4:1101; Vadhan-Raj et al. (1986), *Jrnl. Clin. Oncol.*, 4:137, incorporated herein by reference). These and other studies provide fairly extensive pharmacologic data using highly purified rIFN-gamma, including pertinent pharmacokinetic, toxicologic and scheduling information.

B. Tumor Necrosis Factor

Tumor Necrosis Factor is one of many naturally expressed polypeptides involved in the regulation of growth, differentiation and the function of cells involved in immunity, inflammation and haematopoiesis. The successful cloning of TNF (see, e.g., EPO application publication number 168,214A) has provided formal evidence for its existence and distinction from other factors, and the general availability of this cloned product has greatly facilitated an understanding of its biologic activity. Tumor Necrosis Factor, and the biologically similar Lymphotoxin (LT or TNF-beta), have been the focus of numerous research articles and scientific meetings (see, e.g., *Tumor Necrosis Factor and Related Cytokines,* Ciba Foundation Symposium No. 131, January, 1987). In addition to antitumor effects, a broad spectrum of additional TNF activities have been detailed ranging from regulatory effects on normal cells, to inhibitory effects on various viruses and parasites.

Although the amino acid sequence for TNF-alpha and beta (LT) have only limited homology, they do bind to the same receptor, mediate the same responses and map to the major histocompatibility complex region in man and in mouse (see, e.g., Old (1987) *Nature,* 326:330). However, TNF-alpha is primarily produced by macrophages whereas TNF-beta is primarily of T cell origin. Because TNF-alpha has generally been more readily available, its biological characterization is more advanced. For example, it is now known that many of the activities of TNF mimic the well-known effects of lipopolysaccharide (LPS), for example, tumor haemorrhagic necrosis, fever, shock and activation of neutrophils, indicating that TNF is a mediator of LPS action.

Three lines of evidence directly implicate a role for TNF in macrophage activation: target cells which are resistant to macrophages are also resistant to TNF; target cells resistant to TNF are also resistant to activated macrophages; and TNF antibody inhibits target cell killing by macrophages. However, the mechanism of target cell effects by TNF is not understood. However, it has been suggested that prostaglandins, proteases and free radicals, labilization of lysosomal enzymes and DNA fragmentation may play a role.

Whatever the mechanism of TNF action, certain metabolic inhibitors, heat, IFN's, and in particular, IFN-gamma, are found to greatly potentiate the antitumor actions of TNF (see, e.g., Old, supra). With respect to the basis for TNF-induced anti-tumor effects, clues have emerged from studies on its direct effects on endothelial cells wherein TNF alters growth and morphology, increases synthesis of procoagulant activity and enhances endothelial cell adhesiveness for inflammatory cells.

Several phase I clinical trials of TNF in cancer patients have been started. Anti-cancer effects have been reported with systemic treatment, but these have been somewhat rare in phase I trials. However, such trials are primarily limited to dosaging rather than response rate, an issue approached primarily in connection with phase II trials. However, due to the synergistic effects of combined treatment with TNF and IFN-gamma, there is now considerable interest in such combinations in anti-tumor therapy.

C. Pharmaceutical Compositions

Gamma interferon and/or TNF, in accordance with the present invention, is typically admixed with a pharmaceutically acceptable diluent, such as a sterile aqueous solution, to give a final concentration of about 0.2 to about 2.0 mg/ml with respect to IFN-gamma, and/or about 0.02 to about 0.2 mg/ml with respect to TNF alpha or beta. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility and non-immunogenicity. Such techniques are generally well known in the art as exemplified by the aforementioned *Remington's Pharmaceuticals, supra.*

A preferred interferon gamma composition for parenteral administration includes recombinant derived human IFN-gamma having a sequence corresponding to native human IFN-gamma, either with or without an added n-terminal methionine, and having either the full-length or des (1-3) structure. Such preparations will preferably exhibit a specific activity of on the order of about $2 \times 10^7$ u/mg of protein or greater when tested on A549 cells against encephalomyocarditis virus. It should be appreciated that endotoxin contamination should be kept minimally at a safe level, for example, less than 0.5 ng/mg protein. Moreover, for human administration, preparations should meet sterility, pyrogenicity, general safety, and purity as required by FDA Office of Biologics standards. Most conveniently, IFN-gamma is obtained as a sterile lyophilized powder in vials of desired amounts, for storage at 2° to 8° C. and reconstituted by the addition of a desired amount of sterile water immediately before use.

For use in certain embodiments, for example, for direct instillation into the lungs, preferred compositions include one or more components of surfactant, including phospholipids such as dipalmitoylphosphatidylcholine, dimyristoyl phosphatidylcholine, phosphatidyl glycerol and sphingomyelin, and/or other components such as cholesterol. Additional components such as sufficient salt to render the composition isotonic, as well as one or more surfactant proteins are also preferably included. "Surfactants", as used herein, therefore applies generally to compositions known in the art as biological phospholipid-containing surfactants which include one or more of the foregoing phospholipids. Such phospholipids are generally readily commercially available (e.g., from Sigma Chemical Co.) or preparable by one of various methods known in the art (see, e.g., U.K. Patent Application No. 2,002,631A).

One type of synthetic surfactant which may be employed is that referred to as Exosurf, and described by Durand, et al., supra. In particular, Exosurf is composed of dipalmitoylphosphatidylcholine (greater than 99%, Sigma Chemical Co., St. Louis) 13.5 mg/ml, dispersed in 0.1N NaCl and 2 mM $CaCl_2$ solution with tyloxapol 1 mg/ml. The final concentration of lipid is 15 mg/ml. Dipalmitoylphosphatidylcholine (DPPC) is the major constituent of both human and animal lung surfactant. Hexadecanol is a natural alcohol, and acts as a spreading agent for the DPPC on the air-fluid interface. Tyloxapol is a nonionic surfactant used to disperse the above materials. Both hexadecanol and tyloxapol have been used extensively in medications for human use.

The lipids are dispersed shortly (<30 minutes) before administration by four 15-second bursts of sonication 1 minute apart (Model 185 sonifier, large probe, power level 50, Branson Sonic Power Do., Danbury, Conn.). The temperature of the suspension should not rise about 40° C.

In addition to synthetic surfactant, natural surfactant may be obtained from natural sources such as sheep, calf or the like, e.g., by methods disclosed by Durand, et al., or Kwong, et al., both supra. In general, methods for the isolation of natural surfactant involve extraction of surfactant components from saline lavages of lungs of animals, or from extracts of human amniotic fluid, using organic solvent extraction (see, e.g., Durand et al., supra, or Hallman et al. (1983), Pediatrics, 71:473). After being further purified for pharmaceutical acceptability, the solvent extract may be stored under chloroform or dried under gas, such as $N_2$, and the resultant powder resuspended with physiologic buffers such as saline. Moreover, samples may be flash autoclaved, sealed under sterile conditions, and stored at 4° C. up to 6 months or more, until use.

Where a synthetic surfactant is employed it may be further desired to include surfactant protein components, preferably human surfactant proteins in amounts up to about 1%, such as may be obtained from previously mentioned recombinant methods (PCT publication WO 86/03408) or by protein extraction from natural sources (e.g., amniotic fluid).

Where a liposome-encapsulated IFN-gamma preparation is desired, techniques generally applicable to the preparation of liposome-encapsulated proteins are employed. In general, liposome encapsulation is well known in the art, and numerous techniques may be employed for the lipid encapsulation of IFN-gamma and/or TNF (see, e.g., EPO application publication 160, 266, incorporated herein by reference). Liposomes containing IFN-gamma and/or TNF are prepared from various amphipathic substances including natural and/or synthetic phospholipids. The phospholipids usable to produce liposomes whether uni- or multi-lamellar are numerous and not exhaustively listed herein since they are generally well known in the art. These phospholipids include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides. Most preferable phospholipids for the practice of aspects of the present invention include dimyristoylphosphatidylglycerol (DMPG) and dimyristoylphosphatidylcholine (DMPC). A sterol such as cholesterol in proportions ranging from less than 1% to about 5% or so may be included with phospholipids to produce liposomes of the present invention.

In any case, where surfactant compositions are employed directly in combination with the surfactant-stimulating agents of the present invention, it is generally desirable to admix an appropriate dosage of IFN-gamma, TNF or both, together with surfactant components (e.g., phospholipids, proteins and saline) immediately prior to administration. This provides for retaining the biological agents (IFN-gamma, TNF) and the lipid components each in a highly stable form (e.g., lyophilized powder) pending use.

Based upon an observation of certain apparent additive effects of IFN-gamma with dexamethasone, a potent corticosteroid, in the stimulation of surfactant protein production, it may be advisable in appropriate instances to incorporate corticosteroid therapy. Corticosteroids, where appropriate, are administered either separately or in combination with pharmaceutical compositions of the present invention, in dosages and routes of administration generally employed in the art for corticosteroid therapy of surfactant-deficiency conditions. The various types of corticosteroids, as well as their relative potency, pharmacology, dosaging and the like are well known in the art, see, e.g., Goodman et al. (1985), *The Pharmacological Basis of Therapeutics*, 7th edition, and the Physicians Desk Reference.

D. Dosages and Administration

Minimum effective IFN-gamma and TNF levels for the stimulation of surfactant production in accordance with the present invention is determined herein generally by reference to accepted in vitro assays for surfactant production, including assays for determining the dose-response stimulation of both phosphatidyl choline and surfactant protein production. By comparing the amount of these agents that is required to achieve an effect commensurate with that of proven therapy, such as corticosteroid therapy, an appropriate plasma drug concentration may be more accurately ascertained. A particular assay preferred by the present inventor to demonstrate the effectiveness of IFN-gamma and/or TNF compositions in the treatment of lung membrane diseases, and to compare such actions to a proven therapy, is through the use of a human lung organ culture system. Such organ culture systems allow the advantages of time, reproductability and quantification of IFN-gamma and TNF action. In that they include organ-cultured human lung cells, they are the best predictor of activity in man short of clinical trial. Moreover, in that the IFN-gamma actions are quantifiable in organ culture systems, dosage ranges may be ascertained by comparison to known agents.

The particular assay preferred by the present inventor is that described by Gonzales, et al. (1986), *Jrnl. Clin. Endocrinol. Metab.*, 62:678-691. In this assay, explant cultures of fetal human lung are maintained in organ culture, bathed intermittently in air and culture medium, and treated with varying amounts of test agents for certain lengths of time. After treatment, the measured biologic function, for example, phosphatidyl choline or surfactant protein synthesis, is obtained by subcellular analysis of test versus control tissues.

In such assays, it is typically observed that concentrations as low as 1 ng/ml gamma interferon are sufficient to evoke a stimulation of phosohatidylcholine (PC) synthesis by lung tissue that is commensurate with the effect observed with about 10 nmolar of dexamethasone (approximately 3.5 ng dexamethasone/ml). Even concentrations of IFN-gamma as low as 1 ng/ml elicited a demonstrable effect on PC synthesis. Moreover, a surfactant protein stimulatory effect, similar in magnitude to about 10 nmolar of dexamethasone, was seen with as little as 0.1 ng/ml gamma interferon.

From such comparisons, it is concluded by the present inventor that effective plasma or lung concentrations of IFN-gamma will be on the order of about 0.1 ng/ml upward to levels limited primarily by the onset of toxicity, with maximal benefit being observed with concentrations on the order of 1 to 100 ng/ml. Effective plasma levels of TNF alone are generally about an order of magnitude higher, e.g., about 1 ng/ml upward to levels similarly limited by toxicity considerations. Plasma and hence lung levels reflecting these effective drug concentrations are readily achieved by either daily i.v. infusion, for example, over a 6 to 8 hour period, or daily i.m. administration of dosages of IFN-gamma and/or TNF.

When dosages are given i.m. to an adult, it will generally be desirable to administer daily doses of about 0.1 to about 2.0 mg/m$^2$ of IFN-gamma, preferably on the order of about 0.2 to 0.5 mg/m$^2$, and/or daily doses of TNF of about 1 to about 400 mcg/m$^2$, preferrably about 50 to about 200 mcg/m$^2$, depending upon the appearance of untoward effects such as fever, chills, nausea, etc. This dose, when administered in one or more daily injections, will generally achieve a plasma level sufficient to achieve benefits in accordance with the present invention. It will generally be desirable to administer additional dosages daily until an adequate response such as clearing of symptoms, increase in $pO_2$ levels, etc., is observed. For example, such a regimen is preferably continued until breathing clears and/or endoscopic examination reveals a replenishment of lung surfactant and/or until $pO_2$, $pCO_2$ and pH levels return to normal. Of course, variations in schedule and/or dose are made according to circumstances, for example, where toxicities such as the aforementioned constitutional symptoms appear.

For certain uses in accordance with the present invention, the i.m. route is generally more preferred. This is due to the more consistent IFN-gamma plasma levels generally obtainable by this route, as well as the generally longer plasma half-life observed. Since IFN-gamma therapy in accordance with the present invention is generally indicated until symptoms subside or ameliorate (perhaps up to 7 to 14 days or more), it is generally desirable to maintain effective dose ranges relatively constant. For this reason, i.m. administration is preferred where a parenteral route is employed.

In the treatment of idiopathic RDS, or hyaline membrane disease, it will generally be most convenient to deliver the gamma interferon preparation directly by instillation to the infant's lungs in a suitable pharmaceutical diluent such as saline or surfactant. However, effective administration is in no way limited to instillation, and parenteral routes may be employed as well. Moreover, IFN-gamma compositions may be administered prior to birth, e.g., into the ammiotic fluid, the infant being thus bathed in an IFN-gamma environment.

Instillation of gamma interferon into affected lungs is achieved most readily by preparing a composition of surfactant or saline together with the desired dose prepared, for example, as discussed above. For a premature infant weighing on the order of 1 kilogram, it will generally be desirable to administer about 0.0003 to about 0.05 mg IFN-gamma per day. Where TNF is employed, it will generally be desirable to administer on the order of about one-tenth to about one-fifth as much TNF on a weight basis as IFN-gamma, whether given alone or in combination with IFN-gamma. For larger infants, for example, weighing on the order of 1.5 to 2.0 kilograms, a total daily dose of about 0.003 to about 0.1 mg/day of IFN-gamma and/or about 0.3 to about 10 mcg/day of TNF is administered.

Where surfactant-drug compositions are employed, it will generally be desirable to administer 2-15 ml of surfactant, admixed with the appropriate dose of biologic agent(s), depending on whether an adult or infant is being treated. For example, in the case of a premature infant, the appropriate amount of agent is generally administered together with from 2 to 4 ml total solution. Larger amounts, of course, would be indicated for larger infants or adults, accordingly.

It will be appreciated by those of skill that the foregoing suggested dose ranges are approximations only and effective doses will vary from individual to individual, depending on the age, size or body surface area and degree of untoward effects exhibited by the individual and the particular underlying disease or condition being treated.

As an example, to administer the dose by instillation to a premature infant weighing about 1 kilogram, the following protocol is employed:

1. A pharmaceutical composition is obtained having approximately 0.025 to about 0.05 mg recombinant gamma interferon dispersed in approximately 3 ml of surfactant, saline, or suitable alternative.
2. The infant is endotracheally intubated and the surfactant/interferon composition delivered by syringe through a Brodie adapter fitted to the proximal end of the tube, along with about 7 ml of air.
3. The adapter and syringe are then removed and ventilation established by $O_2$ and resuscitation bag.
4. Doses are repeated in the foregoing fashion periodically to maintain an appropriate plasma level or total daily dose.

Of course, it will be apparent that it is not necessary that the gamma interferon be administered in connection with surfactant, as administration with simple salt solutions such as saline will nevertheless achieve advantages in accordance with the invention. It will also be apparent, in light of the examples which follow, that under certain circumstances it may be desirable to concurrently administer corticosteroids. This is based on the observation that, at least with respect to phosphatidycholine stimulation, corticosteroids act additively with gamma interferon.

The examples which follow illustrate a pharmacologic comparison of recombinant gamma interferon and tumor necrosis factor to dexamethasone in the human fetal lung organ culture system discussed above.

EXAMPLE

A human fetal lung organ culture system was employed to compare the phosphatidylcholine (PC) and protein S-35 stimulatory activity of various agents, including gamma interferon, dexamethasone and tumor necrosis factor.

Human gamma interferon in the des (1-3) form was obtained from recombinant sources as described in EPO patent application publication 146,354, (see also, EPO patent application publication 77,670). Dexamethasone was pharmaceutical grade and the tumor necrosis factor (TNF) was mature hTNF as described in EPO publication 168,214A.

a. Organ Culture

The human lung organ culture was prepared as follows. Lung tissue from 15-24 week gestation therapeutic human abortuses, obtained after elective dilation and evacuation, was minced and placed in organ culture, as in Ballard et al. (1984), *J. Clin. Invest.*, 74:898. Briefly the 1-mm$^3$ pieces were distributed on either side of culture dishes placed on a rocking platform (3 oscillations/min) so that the explants were alternatively exposed to serum-free Waymouth's medium (2 ml/dish) and to an atmosphere of 95% air-5% $CO_2$. Explants were maintained for 1-7 days in medium containing hormones. Fresh medium was added every 24 hr. In some experiments, explants were cultured on pens paper over a grid, as described by Mendelson et al. (1981), *J. Clin. Endocrin. Metab.*, 53, 307. The data shown below was obtained from cells following 7 days of incubation in the presence of drug. Kinetics studies were performed daily b. Determination of Phosphatidyl Choline Synthesis The rate of PC synthesis was measured by incorporation of precursors. Briefly, the radioactive precursor (1 mM [$^3$H] choline in fresh medium) was added during the last 4 h of the culture period, then explants were harvested, rinsed in saline, and frozen overnight. The tissue was sonicated in 0.15 M NaCl, and lipids were extracted by the method of Bligh and Dyer (1959), *Can. Jrnl. Biochem. Physiol.*, 37:94, and PC was isolated by thin layer chromatography. Total PC was reacted with OsO$_4$, then SPC and nonsaturated PC were isolated by thin layer chromatography (TLC), except that the TLC plates were dipped in 0.4M borate in 75% methanol and only developed twice in solvent. Tissue PC and SPC content were determined by ultramicrophosphorus assay. Phospholipid composition and distribution of precursors among phospholipids were determined by single dimension TLC.

The DNA content of the sonicate was determined by fluorometry using diaminobenzoic acid. Statistical analyses were carried out using the paired or unpaired Student's t test, at least squares linear regression, or by analysis of covariance with Newman-Keuls multiple range test. Data are expressed as a mean ±SEM.

c. Determination of SP-35 Protein Production

The change observed in SP-35 production by lung explant cultures was determined generally by the method of Whitsett et al. (1987), *J. Biol. Chem.*, 262:7908, using an ELISA. Briefly, tissue was homogenized in approximately 10 volumes of buffer containing 1 mM phenylmethylsulfonyl fluoride, 10 mM EDTA, 0.1% Nonidet P-40, 50 mM Tris-HCl, pH 7.4. Protein was assessed after a further 100-fold dilution by the method of Lowry in 0.001% Nonidet P-40 using bovine serum albumin diluted in the same buffer as the standards. A two-antibody capture ELISA was utilized to measure SP-35 content following methods described by Katyal and Singh ((1983), *Pediatr. Res.*, 17:439). Goat anti-SP-35 immunoglobulin was prepared by repeated NH$_4$SO$_4$ precipitation and used as the primary capture antibody coated on the plastic ELISA plate at 1:100 dilution. The tissue sample was added in the above buffer followed by the addition of rabbit anti-SP-35 which was used as the second antibody (1:500).

The assay was developed by addition of horseradish peroxidase conjugated goat-anti-rabbit (Miles) using phenylenediamine as substrate. Standard SP-35 and tissue samples were diluted in homogenizing buffer. Standard curves were generated between 1 and 100 ng of purified SP-35 and were entirely linear (regression coefficient=0.90–0.99) over the range used for the assay. Duplicate samples generally varied less than 10%. SP-35 content was determined at several dilutions of each tissue homogenate within a linear portion of the assay curve. Statistical analysis of differences in SP-35 content were determined using an IBM computer using analysis of variance with correction for multiple group comparisons.

d. Assay Results

The results of the foregoing series of experiments determining the effects of IFN-gamma and TNF-alpha, alone or in combination with dexamethasone, on the incorporation of choline into phosphatidylcholine in human fetal lung cells, as well as changes in the SP-35 protein content, is displayed below in Table I, with these data being depicted graphically in FIGS. 1 and 2.

TABLE I

|   |       | PC SYNTHESIS | SP-35 |
|---|-------|--------------|-------|
| 1 | PRE   | 6.61         | 0.1   |
| 2 | CONT  | 8.12         | 4.8   |
| 3 | DEX   | 15.74        | 16.1  |
| 4 | I/1   | 7.81         | 17.6  |
| 5 | I/10  | 9.47         | 18.7  |
| 6 | I/100 | 11.39        | 13.1  |
| 7 | DEX + I | 5.3        | 45.6  |
| 8 | T/1   | 7.14         | 4.3   |
| 9 | T/10  | 9.64         | 10.1  |
| 10 | T/100 | 9.55        | 4.3   |
| 11 | DEX + T | 12.48     | 10.3  |

With reference to Table I and the Figures, values for phosphatidyl choline (PC) and SP-35 production, determined as described above, for explant cultures maintained in media with the indicated drug treatment for a total period of 7 days. PRE refers to the respective values in explants on day 1; CONT is the respective values at 7 days; DEX refers to 10 nmolar dexamethasone; and I/1, I/10 and I/100, refers to concentrations of 0.1, 1.0 and 10 ng/ml of des (1-3) rIFN-gamma, respectively. DEX+I and DEX+T refers to 10 nmolar dexamethesone together with either 10 ng/ml of IFN-gamma or TNF, respectively, and T/1, T/10 and T/100 refers to TNF concentrations of 0.1, 1.0 and 10.0 ng/ml. PC synthesis and SP-35 production are expressed in terms of nmol/4hr/ng DNA and ug/ml DNA, respectively.

Figure 1:
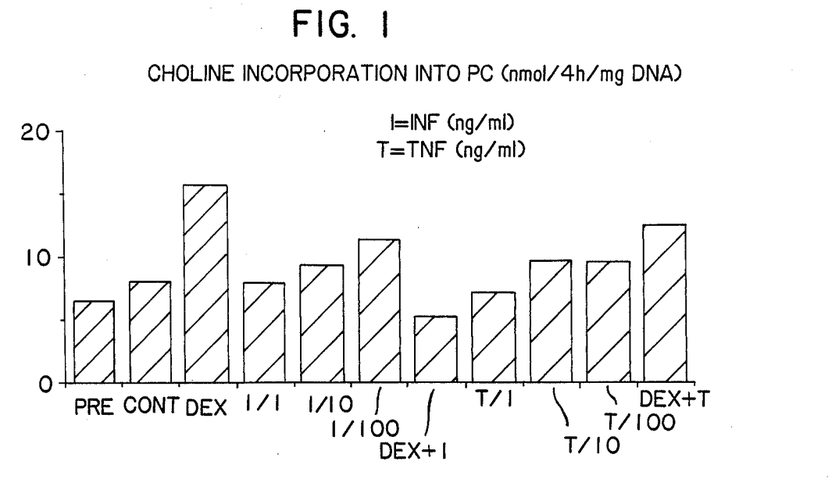
Figure 2:
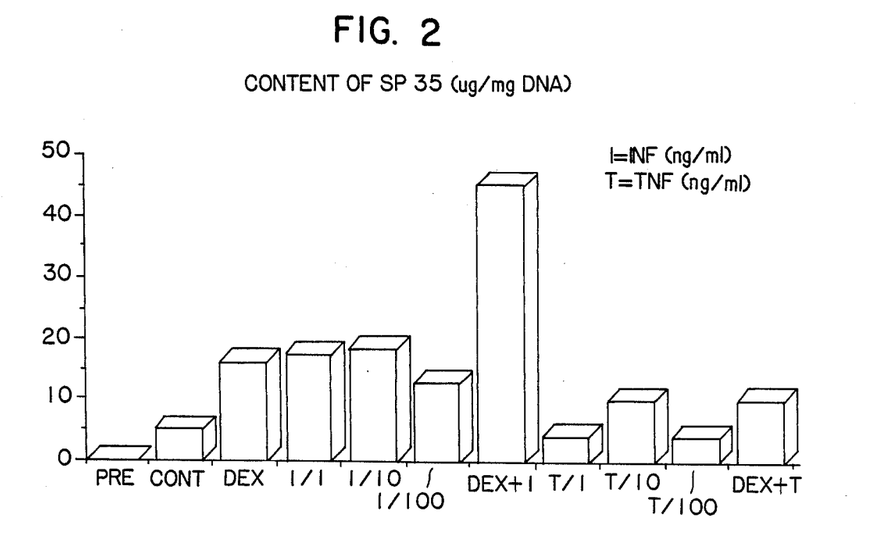
FIG. 2 illustrates graphically the relative effect of the various agents as described in FIG. 1 on surfactant protein production by human lung explants, measured through surfactant protein SP-35 production.

As will be appreciated from the data displayed in Table I and FIGS. 1 and 2, gamma interferon at a concentration of about 1 ng/ml exhibited a PC response almost commensurate with 10 nmolar of dexamethasone. Moreover, in the SP-35 content assay, a dosage concentration as low as 0.1 ng/ml closely paralleled the S-35 inducing activity of dexamethasone. Curiously, combinations of dexamethasone with interferon were synergistic in terms of SP-35 stimulation, yet seemingly inhibitory of each other in terms of PC synthesis. It will also be appreciated that concentrations of TNF on the order of or greater than 1 ng/ml resulted in enhanced PC synthesis as well as varying degrees of SP-35 enhancement.

It will be apparent to those of skill in the art that many modifications and changes in the present invention as detailed herein may be made without departing from the scope intended. For example, changes may be made in doses and relative amounts of components in view of the particular circumstances, such changes being apparent to those of skill in the art in light of the present specification. Moreover, it is likely that new and improved INF-gamma and/or TNF substances will be developed and the use of such improved compositions may be employed in the practice of the present invention so long as they retain traditional IFN-gamma actions as described herein or known in the art. These and all other equivalent modifications and changes are included within the scope of the present invention as defined by the following claims.

What is claimed is:

1. A method of treating an individual having or at risk of having idiopathic respiratory distress to increase the surfactant content of the individual's lungs, the method comprising the steps of:
   (a) identifying an individual whose lungs may be in need of an increased level of surfactant; and
   (b) administering to the individual a composition which includes a therapeutically effective amount of gamma interferon or TNF.

2. The method of claim 1 wherein the individual is identified as having a respiratory distress syndrome.

3. The method of claim 2 wherein the individual is an infant.

4. The method of claim 3 wherein the infant is identified as having hyaline membrane disease.

5. The method of claim 4 wherein the composition is administered in utero prior to birth; or parenterally or by instillation after birth.

6. The method of claim 1 wherein the individual is an adult identified as having an adult respiratory distress syndrome.

7. The method of claim 1 wherein the composition is administered parenterally.

8. The method of claim 6 wherein the composition is administered intramuscularly.

9. The method of claim 1 further comprising administering a phospholipid-containing surfactant to the individual's lungs by instillation.

10. The method of claim 9 wherein said composition includes a therapeutically effective amount of gamma interferon.

11. The method of claim 1 further comprising administering to the individual a therapeutically effective amount of a corticosteroid.

12. The method of claim 1 wherein the composition comprises a therapeutically effective amount of IFN-gamma and TNF.

13. The method of claim 9 wherein said phospholipid-containing surfactant comprises a synthetic surfactant.

14. The method of claim 1 wherein a total daily dose of between 0.01 and 2 mg of gamma interferon or between 1 and 400 mcg TNF per $m^2$ total body surface area is administered to the patient.

15. The method of claim 1, wherein said individual is a fetus, and said administration is performed in utero.

* * * * *